United States Patent
Prince (10) Patent No.: US 9,049,433 B1
(45) Date of Patent: Jun. 2, 2015

(54) HIGH-SPEED RAILROAD INSPECTION USING COORDINATED 3D CAMERAS

(76) Inventor: John H. Prince, Los Altos, CA (US)

(*) Notice: Subject to any disclaimer, the term of this patent is extended or adjusted under 35 U.S.C. 154(b) by 459 days.

(21) Appl. No.: 13/374,678

(22) Filed: Jan. 6, 2012

(51) Int. Cl.
| H04N 13/02 | (2006.01) |
| H04N 7/18 | (2006.01) |
| G06K 9/00 | (2006.01) |
| B61K 9/10 | (2006.01) |
| G01N 21/17 | (2006.01) |
| G06T 7/00 | (2006.01) |
| B61L 23/04 | (2006.01) |

(52) U.S. Cl.
CPC .............. *H04N 13/0239* (2013.01); *B61K 9/10* (2013.01); *G06T 7/0004* (2013.01); *G06T 7/0077* (2013.01); *G01N 2021/1785* (2013.01); *G01N 2291/2623* (2013.01); *H04N 13/0242* (2013.01); *B61L 23/042* (2013.01); *B61L 23/045* (2013.01)

(58) Field of Classification Search
CPC .......... H04N 13/0239; H04N 13/0296; H04N 7/181; B60R 1/00; B61K 9/08; B61L 23/042; B61L 23/045; G01N 2021/1785; G01N 21/8851; G01N 2291/2623; G06T 7/0077; G06T 7/0004
USPC .............................. 348/47, 148; 382/104, 154
See application file for complete search history.

(56) References Cited

U.S. PATENT DOCUMENTS

| 5,282,255 | A | | 1/1994 | Bovik et al. .................... 382/239 |
| 5,956,077 | A | * | 9/1999 | Qureshi et al. .................. 348/82 |
| 6,611,343 | B1 | | 8/2003 | Frankowski ................... 356/371 |
| 7,032,458 | B2 | * | 4/2006 | Tanaka .............................. 73/800 |
| 7,389,694 | B1 | * | 6/2008 | Hay et al. ......................... 73/635 |
| 7,616,329 | B2 | * | 11/2009 | Villar et al. .................... 356/625 |
| 7,716,010 | B2 | * | 5/2010 | Pelletier ......................... 702/158 |
| 2004/0263624 | A1 | * | 12/2004 | Nejikovsky et al. .......... 348/148 |
| 2008/0063261 | A1 | * | 3/2008 | Kang ............................. 382/154 |
| 2009/0045326 | A1 | | 2/2009 | Sato et al. ...................... 250/216 |
| 2010/0017060 | A1 | | 1/2010 | Zhang et al. ..................... 701/41 |
| 2010/0245799 | A1 | | 9/2010 | Kim et al. .......................... 366/3 |
| 2011/0181721 | A1 | * | 7/2011 | Bloom et al. ................. 348/148 |
| 2012/0081519 | A1 | * | 4/2012 | Goma et al. .................... 348/47 |
| 2012/0188342 | A1 | * | 7/2012 | Gervautz et al. ................ 348/46 |

FOREIGN PATENT DOCUMENTS

CN 101639452 A * 2/2010 ............. G01N 21/88

\* cited by examiner

*Primary Examiner* — Gelek W Topgyal (57) ABSTRACT

To emulate the 3D visual acuity of an individual track-walker, matched pairs of cameras (which simulate our human eyes) are mounted on a moving vehicle above the tracks. The cameras are mounted both transversely and longitudinally, to create 3D images in two orthogonal orientations, which helps to eliminate visual voids. The location and orientation of each pair of cameras is determined by its specific task, in the present case: (i) to examine each left or right rail for anomalies (two pairs), and (ii) to examine every tie for damage (at least one pair). The camera pairs enable measurements such as defect depth and track width variations. The images are compressed in real time for local storage or high-speed transmission for remote display. The basic arrangement of cameras can be amplified or modified as necessary to circumstances.

18 Claims, 6 Drawing Sheets

HIGH-SPEED RAILROAD INSPECTION USING COORDINATED 3D CAMERAS

BACKGROUND OF THE INVENTION

1. Field of the Invention

This invention relates to the in-depth inspection of objects which may hitherto have been examined as flat. The addition of an extra dimension replicates the human eye and contributes to a sense of depth, and adding valuable information for the inspection of diverse objects, in this case railroad ties and track. These objects can be instantaneously compared and sorted against three-dimensional (3D) templates which may reflect the ideal for that particular object. With advanced object recognition software inspection can be done at high speed and with great accuracy. The images can also be compressed in real time for high-speed transmission for remote display or analysis, or sent for compact storage. This invention is here applicable in the visible, infra-red, microwave and ultra-violet portions of the spectrum. It may apply also to sonar or ultrasound.

2. Description of the Related Art

Because rail inspection has traditionally been done by "walking the tracks"—which is to say by a person carrying a notepad and visually assessing such items as missing bolts and damaged rails, it has been slow. It has been dependent on the visual (3D) acuity and judgment of the individual. In many areas of the world it is still done that way. Recently, more advanced techniques which depend on several cameras affixed to specialized rail-mounted trucks have been used. Their recorded (2D) images of ties and tracks are later examined and compared by individuals in their offices. However the transfer of data, the interpretation on charts and maps, can still be laborious and lengthy. There are also time-consuming tactile approaches.

A more complex approach to railroad inspection is possible through laser scanning. In the instances where laser scanning is used (such as on jet turbine blades) the technology requires highly reflective (i.e. specular) surfaces and computer reconstruction to create (measurable) 3D images. In the present instance such specular surfaces do not obtain from rails or ties for the creation of 3D images. Laser scanning is also computationally expensive and reconstruction to create 3D images is lengthy.

There are 140,000 miles of standard-gauge mainline track in North America with twenty-two million standard length rail sections riding on half a billion ties. Some of these units are more than fifty years old. A single track failure can be catastrophic for passengers, goods, equipment and environment. With shipping increasing as well as cargo loading, continuous examination of this rail and its maintenance is a very necessary task. It is no longer thinkable to do any part of this by "walking the tracks" or even by running slow-moving trucks that can interfere with rail traffic. In addition there are a further 160,000 miles of lesser-used tracks to monitor.

What is required is a simple, robust, fast inspection system which is self-contained and can be easily mounted on any railroad carriage, freight-car or engine. It should travel at normal speeds and be remotely monitorable. It should also be low-cost initially and easy in maintenance.

In the present invention we have the opportunity to achieve these ideals. We have the opportunity to restore the visual (3D) acuity of the original track-walker, accelerate the imaging, greatly reduce the cost and all-but eliminate interpretive error. In due course—within a time-frame measured in months rather than years—this invention can provide the storage (and the instant retrievability) to identify and track every single tie and rail section of the entire railroad system, while using integral GPS coordinates for their precise location.

We are enabled in this endeavor by the immense recent increase in computing power, storage capacity and communication ability in electronics, easing our (major) tasks of assembling the 3D components and contributing the algorithms to make it feasible.

SUMMARY OF THE INVENTION

To emulate the 3D visual acuity of the individual trackwalker, pairs of cameras (which simulate our human eyes) are mounted on a moving vehicle above the tracks. The cameras are mounted both transversely and longitudinally, to create 3D images in two orthogonal orientations, helping to eliminate visual voids. The location and orientation of each pair of cameras is determined by its specific task, in the present case: (i) to examine each left or right rail for anomalies (two pairs), and (ii) to examine every tie for damage (at least one pair). This basic arrangement can be amplified or modified as necessary to circumstances.

The cameras can be "trained" in discrete pairs to angle in and focus at certain distances for the recognition of anomalies. These anomalies will be specific to certain types of rails—which may be assembled in standard (39' or 78') sections or continuously welded: and to certain types of ties—wooden (90% in USA), steel, concrete or plastic; the wood itself can be varied—oak, Douglas fir, jarra, creosoted, etc.

The recognition of anomalies will be related to known templates (reflecting acceptable standards) for particular track sections. Anomalies will be noted and (depending on their severity) will be available for instant visual review.

In addition to viewing (particularly) the ties as flat the software can accurately calculate the depth of certain anomalies, as will be shown.

BRIEF DESCRIPTION OF THE DRAWINGS

This invention, with its further advantages described below, may be understood best by relating the descriptions to the appended drawings, where like reference numerals identify like elements, and in which.

DETAILED DESCRIPTION OF THE INVENTION

In order to emulate the depth-perception and 3D acuity of pairs of human eyes, the cameras come as pairs with highly compact electronics integral to their function. Two cameras forming each pair are separated by a distance determined by their application and work as a single unit. Each unit is adapted to its specific role (as described below).

Figure 1:
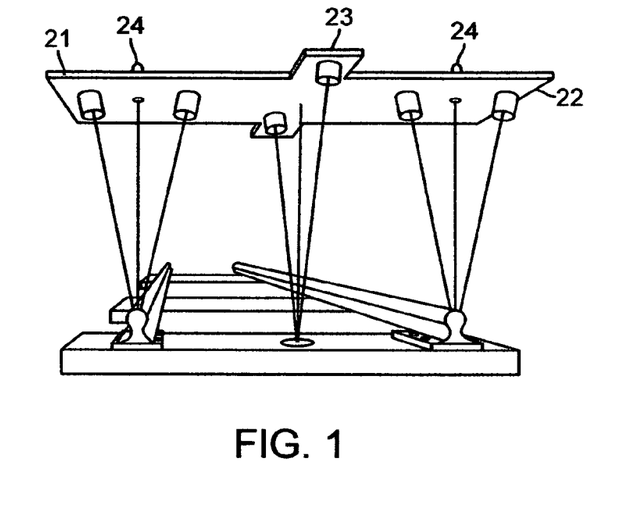
FIG. 1 shows an overall system for examining a railroad track, consisting of pairs of cameras held on a rigid frame, mounted onto a railcar at some fixed distance above the tracks. Some of these cameras will be for transverse and some for longitudinal inspection, creating holistic images of each rail section.

FIG. 1 shows a bilaterally symmetrical structure 21 for holding three sets (pairs) of cameras, or six cameras. This consists of a transverse member 22 and a longitudinal member 23 of sufficient stiffness and damping to hold the three sets of cameras rigid and resonance-free when mounted. Two projections 24 are bolts or clamps for mounting the structure onto a suitable railcar. For standard gauge tracks the length of transverse member 22 is about 84" and the length of longitudinal member 23 is about 24".

Figure 2:
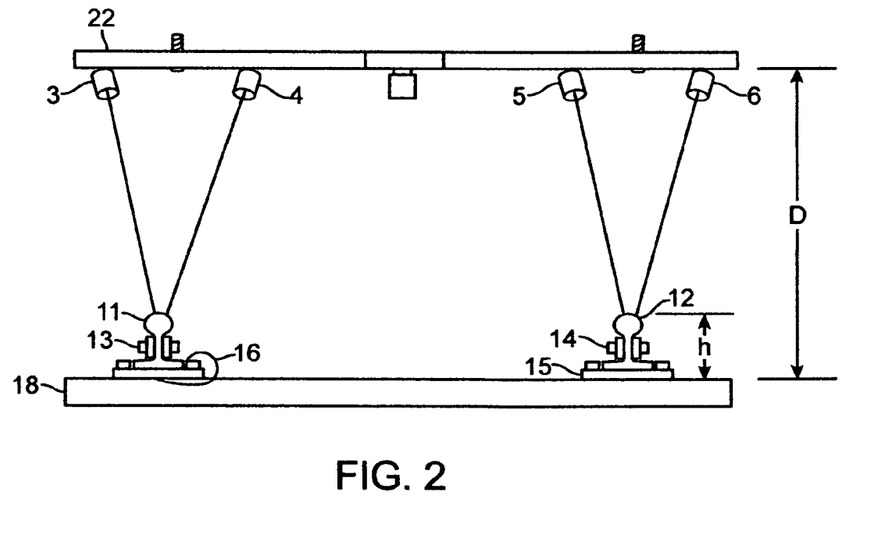
FIG. 2 shows two pairs of cameras mounted transversely for simultaneously inspecting both left and right rails 11 and 12.

FIG. 2 shows the arrangement of the transverse cameras on structural member 22. The distance (D) of structural member 22 above ties 18 we have (arbitrarily) fixed at about 40" (or one meter for ease of calculation). The cameras 3 and 4 are arranged symmetrically above the left rail 11, and the cameras 5 and 6 are arranged symmetrically above the right rail 12. The cameras are angled inwards so that they face (and focus) on intermediate points between the tops of the rails 11 and the bottoms of the base-plates 15. This distance (h) is about 6". It is also the depth of field of the cameras and is necessary for clear imaging over that distance. Also shown in this diagram are subjects for inspection—nuts 13, tie-plates 14, base-plates 15, Pandrol clips 16 and ties 18. For inspection all of these objects fall (necessarily) within the respective fields of view of each pair of cameras.

Figure 3:
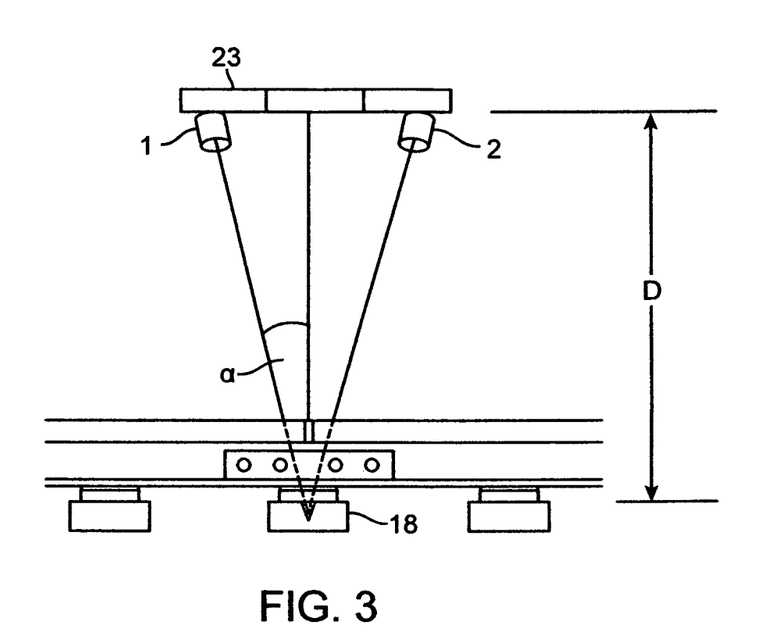
FIG. 3 shows a pair of cameras 1 and 2 mounted longitudinally for inspecting ties.

FIG. 3 shows the arrangement of cameras 1 and 2. These are mounted as a unit onto longitudinal member 23 and are angled inwards to focus on the tops of ties 18. The field of view of cameras 1 and 2 covers the distance between rails 11 and 12. With our (chosen) 40" height (D) of the cameras above the ties the field of view will be 70°, enough to cover the 4' 8½" (inner) width of standard gauge track. The depth of field of cameras 1 and 2 is fixed here at f/2 for accurate calculation of depth and will range between 40" and 48".

Figure 4:
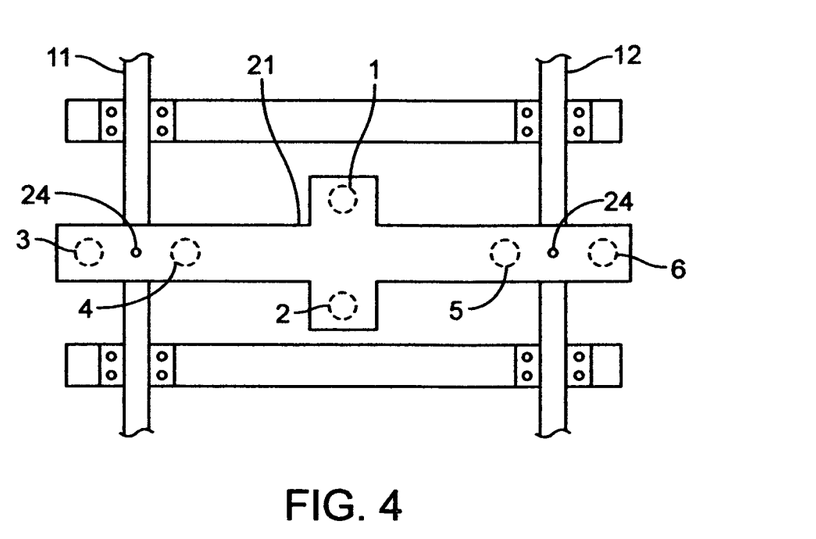
FIG. 4 shows the top view of the camera layout, a symmetric cross 21 with bolts 24 for mounting to a rail-car.

FIG. 4 shows a top view of the structure 21 which holds the cameras. The mounting bolts (or clamps) 24 are shown. These must have some adjustment so that the height (D) is properly maintained between railcars. For optimum results the structure 21 must also be centered on a railcar so that the transverse cameras (in pairs) 3 and 4, then 5 and 6, symmetrically straddle rails 11 and 12. The distance between the centers of the camera pairs is 4' 11" for standard gauge tracks. (Travelling on certain curves or over points the cameras may not straddle perfectly, but within certain limits the images will adapt for calculation).

Figure 5:
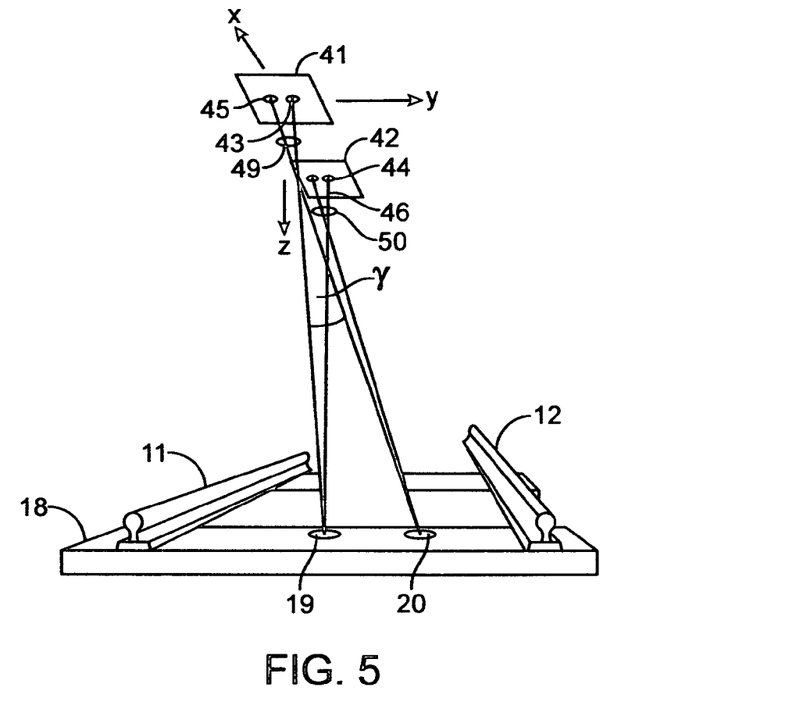
FIG. 5 shows how images of anomalies on a tie 18 are displaced on detectors 41 and 42 as the angle from normal is increased.

In FIG. 5 we look at detector 41 (of camera 1) and detector 42 (of camera 2). The pixel clusters 43 and 44 are the two images of an anomaly 19 in tie 18 on the z-axis directly beneath the cameras. Similarly, the pixel clusters 45 and 46 are the two images on the detectors of an anomaly 20 which is off the z-axis by an angle γ.

For the depth of feature 20 which is off-axis we must multiply the apparent pixel shift by the cosine of γ to get the depth. We will discuss these images later.

Figure 6:
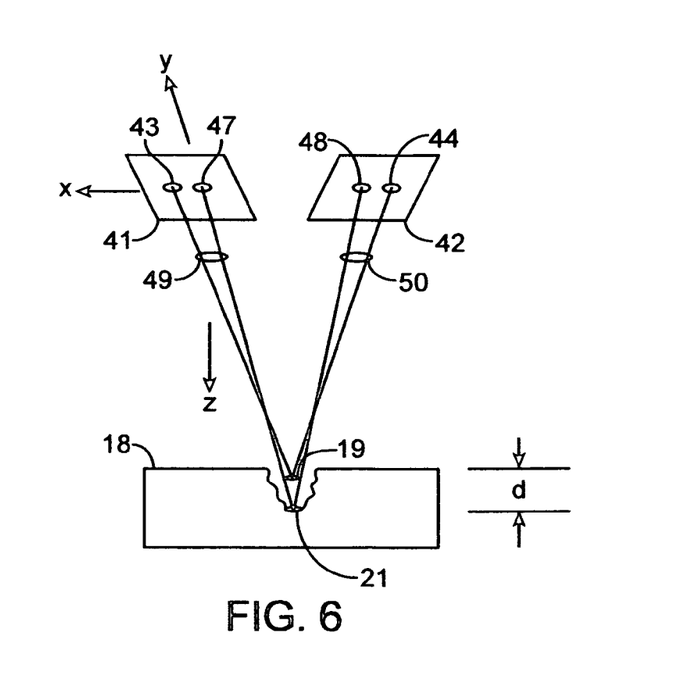
FIG. 6 shows the effect of anomaly depth (d) in tie 18 on the placement of images in detectors 41 and 42.

FIG. 6 is a diagram to show how depth is calculated in relation to cracks, erosion, and other miscellaneous features such as 19 and 21 in ties.

Figure 7:
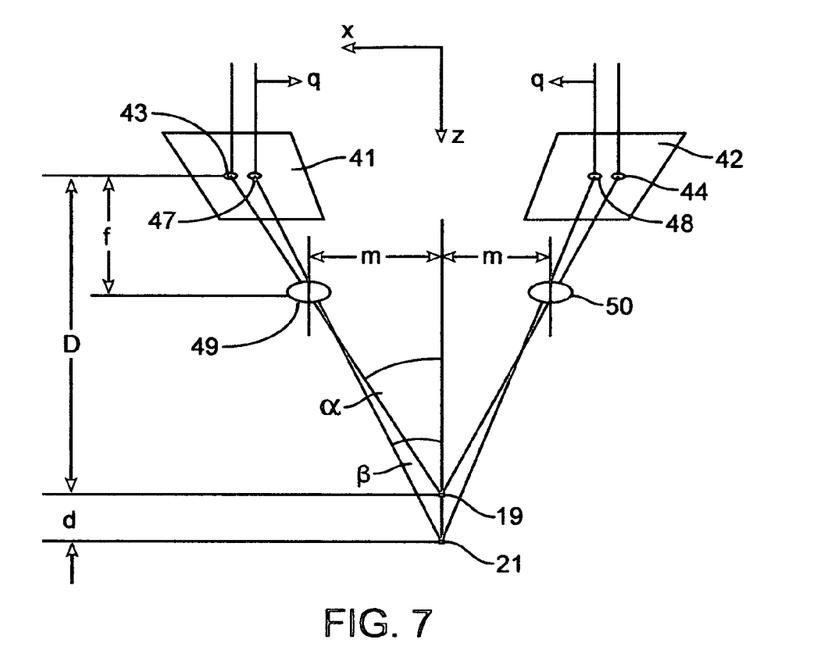
FIG. 7 shows how the depth of an anomaly can be calculated by the displacement of an image as seen simultaneously on detectors 41 and 42.

FIG. 7 is a diagram for calculating the depth of a crack 19 in tie 18. This diagram shows how the images of this crack shift on detector 42 (of camera 2) and also detector 41 (of camera 1) depending on the depth (d) of the crack. In this example, if the depth this crack is ⅛" (or 3 mm) the focused images will shift laterally by 28μ or 14 pixels.

Referring back to FIG. 2 we see how a rail 12 is imaged by two cameras 5 and 6. The cameras subtend a half-angle of 14°. When displayed, this will show as a single 3D picture of the rail even though the images are taken from two quite different viewpoints. (This is akin to looking at a finger 5" in front of one's eyes, in which one's finger is perfectly and singularly imaged, though the eyes here also subtend the same half-angle). This 3D perspective allows defects in the rails, like brinelling and spalling, as well as cracks, to be very clearly seen. Also shown is how the imaging system "wraps around" the rail to give a 210° view.

Figure 9:
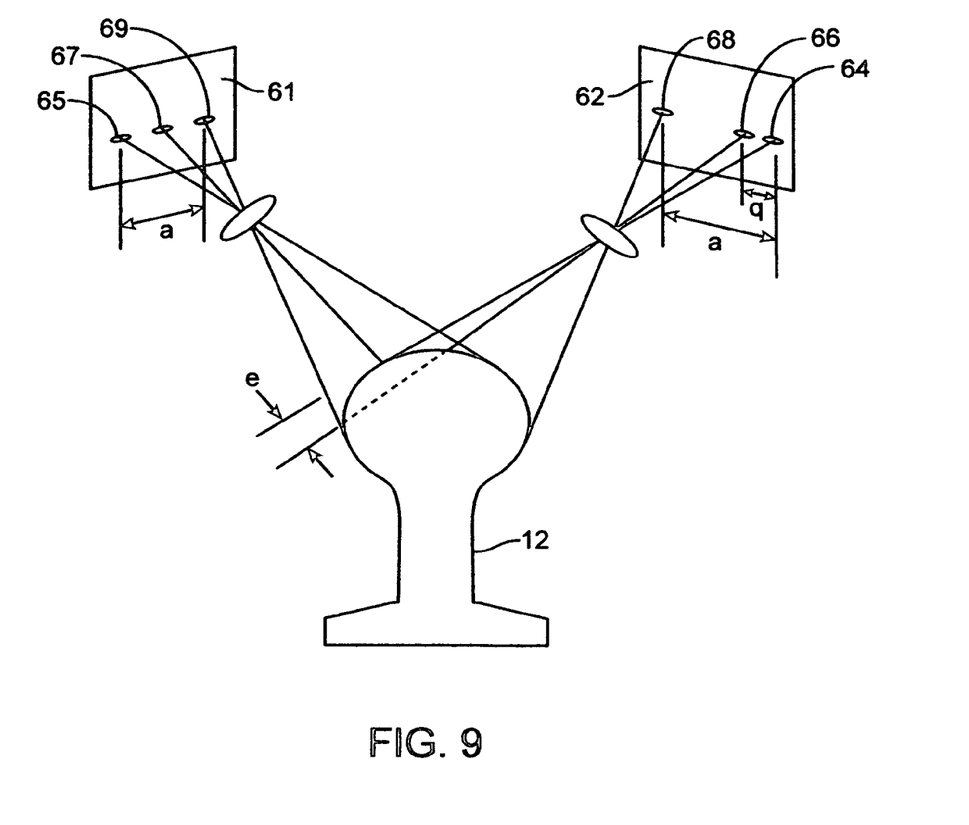
FIG. 9 shows how erosion (e) on the inner side of rail 12 can be measured by simultaneous observation on detectors 61 (in camera 5) and 62 (in camera 6).

In FIG. 9 we show how a 3D perspective allows a direct calculation for erosion.

In FIG. 9 we see a cross section of rail 12, whose features are imaged on detector 61 (of camera 5) and detector 62 (of camera 6). Pixel clusters are shown imaging the rail-head 12. On the two detectors, the clusters 68 and 64 image where the rail section should be; however the clusters 68 and 66 image what the rail section has become. Erosion (e) is shown with reference to a template of that rail section. A simple calculation shows that for ⅛" of erosion the displacement of clusters is 56 pixels, with the pixels imaging the rail section moving from point 64 to point 66 on detector 62. These offsets are along the y-axes of the detectors.

As will be described in detail later, these offsets (or displacements) are well within the resolution of the cameras and enough to calculate the depths of features and profiles closely.

This camera arrangement 3 and 4 with 5 and 6 also allows the precise calculation of the distance between the rails 11 and 12.

In order to obtain accurate measurements we turn to algorithms for camera alignment and feature recognition.

It has already been noted that we have picked a height above the roadbed of 40" for the cameras. We could standardize at any similar height. It would be of benefit to make this a universal reference.

To create 3D images with minimum computation the cameras should come as matched pairs. Most conveniently they will use identical detectors and have identical optics.

For camera pairs we can enumerate certain physical degrees of freedom—focal length, aperture, zoom, x, y and z, and pitch, roll and yaw. All degrees of freedom must then be adjusted together so that cameras in pairs match each other as closely as possible. As examples, the pose of the cameras, i.e. their axes, should intersect; apertures also should be adjusted to give matching light intensity on the detectors, etc.

This first step for each pair of cameras is primary alignment. We have fixed the height of cameras 1 and 2 above the track bed at 40". Their primary function is to look at ties. Since these will all lie on the same plane 40 we can use a flat target (with fiducial marks and lines) at the same distance (40") from the cameras for alignment. By comparing images side by side on a 2D display (against their fiducial marks and lines), or simply overlapping on a 3D screen, the two images can be brought (visually, through manual adjustment) into close correspondence in all their degrees of freedom.

Similarly for camera pairs 3 and 4, then 5 and 6, using a target simulating a rail at 37", which is the median height of the rail above the ties.

With proper adjustments on either the cameras or the mountings, and a good imaging screen nearby, the primary alignment processes for all pairs of cameras can (usually) be done in minutes.

A simple recipe for bringing the images from each pair of cameras into close correspondence can be performed in Matlab. It depends on accurately choosing (at least two) well-separated matching features in the two images. In the case of the ties this could be the images of cracks such as 19 and 20. The median (estimated) pixel positions must be delivered to the program below into the two functions ginput2( )(below) by the user.

We note that in the matching algorithms below we use the local coordinates of the detectors (rather than the global coordinates discussed later for calculations). That is, that when our alignments are carried out to a sufficient degree point ($x_i$, $y_i$), of detector 41 will correspond (almost) exactly to point ($x_i$, $y_i$) of detector 42.

alignment.m
% load input images
I1=double(imread('left.jpg'));
[h1 w1 d1]=size(I1);
I2=double(imread('right.jpg'));
[h2 w2 d2]=size(I2);
% show input images and prompt for correspondences
figure; subplot(1,2,1); image(I1/255); axis image; hold on;
title('first input image');
[X1 Y1]=ginput2(2); % get two points from the user
subplot(1,2,2); image(I2/255); axis image; hold on;
title('second input image');
[X2 Y2]=ginput2(2); % get two points from the user
% estimate parameter vector (t)
Z=[X2' Y2'; Y2'-X2'; 1 1 0 0; 0 0 1 1]';
xp=[X1;Y1];
t=Z \ xp; % solve the linear system
a=t(1); %=s cos(alpha)
b=t(2); %=s sin(alpha)
tx=t(3);
ty=t(4);
% construct transformation matrix (T)
T=[a b tx; -b a ty; 0 0 1];
% warp incoming corners to determine the size of the output image (in to out)
cp=T*[1 1 w2 w2; 1 h2 1 h2; 1 1 1 1];
Xpr=min([cp(1,:) 0]): max([cp(1,:) w1]); % min x: max x
Ypr=min([cp(2,:) 0]): max([cp(2,:) h1]); % min y: max y
[Xp,Yp]=ndgrid(Xpr,Ypr);
[wp hp]=size(Xp); %=size(Yp)
% do backwards transform (from out to in)
X=T \ [Xp(:) Yp(:) ones(wp*hp,1)]'; % warp
% re-sample pixel values with bilinear interpolation
clear Ip;
xI=reshape(X(1,:),wp,hp)';
yI=reshape(X(2,:),wp,hp)';
Ip(:,:,1)=interp2(I2(:,:,1), xI, yI, '*bilinear'); % red
Ip(:,:,2)=interp2(I2(:,:,2), xI, yI, '*bilinear'); % green
Ip(:,:,3)=interp2(I2(:,:,3), xI, yI, '*bilinear'); % blue
% offset original image from warped image using local coordinates
offset=-round([min([cp(1,:) 0]) min([cp(2,:) 0])]);
Ip(1+offset(2):h1+offset(2),1+offset(1):w1+offset(1),:)=double(I1(1:h1,1:w1,:));
% show the results
figure; image(Ip/255); axis image;
title('aligned images');

Having the images now lined up visually to within a few pixels may be adequate for railroad tie inspection. However it may not be adequate for estimating items such as erosion or seeing fine cracks in rails.

Therefore we must delve into a more accurate secondary alignment using a "feature-based" approach. In general, for feature selection, any of a number of edge detection algorithms can be used, such as: J. Canny, "A Computational Approach to Edge Detection," *IEEE Transactions on Pattern Analysis and Machine Intelligence*, Vol. PAM1-8, No. 6, 1986, pp. 679-698). We can apply this to features we have already chosen, using the local coordinates of detectors 41 and 42.

We use a sum of squares function $E_{SSD}(u)$ (See Richard Szeliski, December 2006) to look for the minimum difference between individual (noted) features on detectors 41 and 42:

$$E_{SSD}(u)=\Sigma_i[I_1(x_i+u)-I_0(x_i)]^2=\Sigma_i(e_i)^2$$

Where u=(u, v) is the feature displacement on the two detectors (using local coordinates) and $e_i=I_1(x_i+u)-I_0(x_i)$ is the error function or feature displacement offset within the detecting areas ($I_0$ being the reference feature image on detector 41 and $I_1$ the sample image on detector 42).

The sum of squared differences function $E_{SSD}(u)$ above can also be written as a Fourier transform:

$$F\{E_{SSD}(u)\}=F\{\Sigma_i[I_1(xi+u)-I_0(xi)]^2\}=\delta_{(f)}\Sigma_i I_1^2(xi)+I_0^2(xi)]-2I_0(f)I_1^*(f)$$

The right-hand expression shows how ESSD(u) can be computed by subtracting twice the correlation function (the last term) from the sum of the energies of the two images (the first term). We can also use the discrete cosine transform (DCT-2) if we want to correlate larger pixel areas.

This alignment of x and y coordinates will bring the two detectors 41 and 42 onto almost identical points ($x_i$, $y_i$) on their local x-y planes, differing only by their global offsets m and −m on the x-axis, as in FIG. 7. This alignment applies sequentially to all camera sets 1 and 2, then 3 and 4, then 5 and 6.

With the cameras aligned and secured in their locations we can estimate with some precision variations in the geometry of the rails and also the size and shape of defects in the ties.

For example, in FIG. 6 we show a crack 19 in tie 18. The two images of the crack 19 (where the surface of the tie should be) are located at points 43 and 44 on detectors 41 and 42 respectively. In a momentary shift (the train is moving) the two images now find themselves displaced to points 47 and 48, showing a deepening (d) of the crack 21. We can calculate this deepening (d) with fair accuracy.

This is shown in FIG. 7. If f is the focal length of the cameras (the distance from lens 49 to detector, and from lens 50 to detector 42, such as 35 mm), D is the height of the cameras above the ties (about 40", or 1 meter), m is the distance of the cameras from their centerline (about 10"), and q is the (small) pixel displacement on the two detectors, then the depth (d) of a feature is approximately given by $$d = \frac{qD^2}{mf}$$

As an example of this calculation, if the displacement (q) is 14 pixels then the depth (d) of the crack will be ⅛" (3 mm). This displacement (q) is well within the resolution of the cameras and allows for a fast and accurate estimate of depth.

We note here that we have used a symmetric z-axis pose for the cameras. In the case of off-axis estimations and unequal values of q we can take their average multiplied by cos γ to derive depth. The angle γ is shown in FIG. 5.

A sum of such images and measurements can provide a depth and outline map of cracks and anomalies in ties which (for evaluation) can be compared with templates stored in computer memory for each particular section and type of track.

Figure 8:
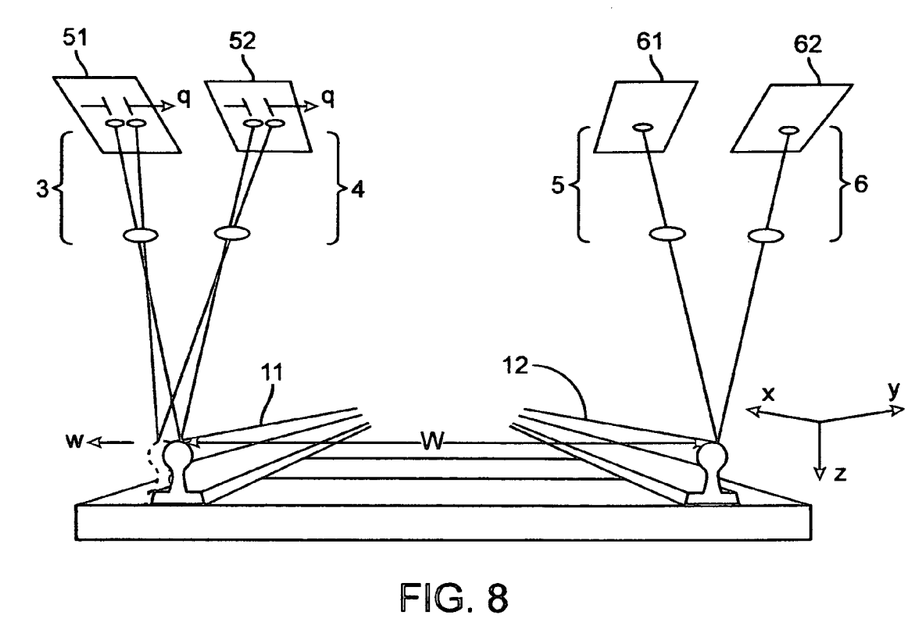
FIG. 8 shows how the width of the rails (W) can be calculated instantaneously and accurately by variances in the images projected onto detectors 51, 52, 61 and 62.

As a further example in FIG. 8, we can estimate variances in the width of the tracks. For standard gauge this width (W) should be 4' 8½", but can vary by ±½". A straightforward calculation shows that for an increase in the width of the track (w) from the standard width (W) the pixel displacement (q) will be $$q = fw/(D-f)$$

If the increase in the width (w) is ⅛" then the pixel shift (q) will be 54. This is well within the resolution of the cameras and can yield instantaneous and accurate values for the width of the tracks while the cameras are moving. In fact if we allow a pixel shift of ±5 as the limiting resolution, the track width (W) can be estimated to within ±0.010".

In FIG. 8 this variance in width (w) noted on detectors 51 and 52 must be taken in conjunction with similar variances noted on detectors 61 and 62—and here we show none. If variances show up in both sets equally then it's probable that the train is either on a curve or going over points, both situations being accountable through software.

In FIG. 8 it is noted that the pixel displacements (q) are the same (or similar) on detectors 51 and 52 and in the same direction. This will represent a true variance in the width (w) of the tracks. If on the other hand the pixels displacements are both inwards (as is shown in FIG. 6) then this will represent a dip in the tracks, and if they are both outwards this will represent a bump.

In FIG. 8 there can arise (less usual) situations where the pixel displacements are simultaneously unequal and opposite between detectors 51 and 52, and also 61 and 62, representing variances in width (w) as well as dips and bumps. These situations are handled in software as exceptions.

In FIG. 9 is shown a method of estimating erosion (e) (typically on the inner side) of a track. Here a profile of track 12 is seen on detectors 61 and 62. The original profile is stored in memory for that particular track section. Comparing (on detector 62) the position of edge pixels 64 (as they should have appeared in memory) with the position of edge pixels 66 (as they actually appear) there is a displacement of pixels (q). The erosion (e) can be calculated simply from $$e = q/f(D-f)$$

where D is the distance from the cameras to the railhead (34") and f is the focal length of the cameras (35 mm).

Assuming a symmetrical rail section an even simpler method of measuring erosion (e) is shown in FIG. 9. With a symmetrical rail 12 the distance between the edge pixels 65 and 69 (on detector 61) and between edge pixels 62 and 64 (on detector 62) should be equal. Here we see there is a difference (q) which represents the displacement of edge pixels from 64 to 66 due to erosion (e). We can calculate erosion (e) quickly from the formula above.

Although it is not shown in FIG. 9 the ability of the two detectors 61 and 62 to simultaneously image the rail head and rail base allows them to measure twist or leaning in rail 12 in a formula equivalent to the one above. The change in alignment between the two lower rail-edges is seen as a pixel shift in their images, allowing a calculation of the twist or lean to an accuracy of ±0.010".

Since we are discussing the transmission of measurements in real time some note must be made of the method.

In the present example a set of six coordinated cameras is mounted on a typical carriage, railcar or engine travelling at a nominal speed of (say) 60 miles per hour. Each pair of cameras is self-contained with battery, GPS locator, processor, software, and transmitter as in FIG. 10. Each pair has been calibrated for its particular function, to look at either rails or ties. At the speed of 60 miles per hour (88' per second) cameras 1 and 2 view 54 ties per second; each pair of cameras 3 and 4, then 5 and 6, view just over two lengths of standard 39' rail per second.

It is possible also to use pre-combined 3D cameras, as packaged within the size of a cell-phone. Because of a smaller vergence angle these will not be able to calculate depth or width as accurately.

For illumination in all conditions all cameras come twinned with bright white LED sources. Other illumination and colors are also possible.

At 60 mph cameras 1 and 2 now have (about) 4 ms to look at each tie, with a further 7 ms to compute depth profiles and search libraries for matches—totaling 11 ms per tie. Cameras 3, 4, 5 and 6 have 44 ms to look at each 39' rail, to check for erratic bolts, nuts and Pandrol clips. All camera pairs are synchronized for holistic viewing of each railroad section. Each camera's speed is 60 frames per second (at 1080p resolution)—enough at 60 miles per hour to create one frame per tie. The conspectus of all cameras is well within the capacity of the on-board computers, as noted below.

Cameras 1 and 2 can also look at a broader section of track. A 70° field of view allows them to see three ties at a time, at 60 mph allowing 33 ms for noting and comparing anomalies. Instead, if the cameras are mounted on a high-speed (180 mph) train three ties will be examined in 11 ms. (The resolution of the GPS system here may limit the coordinates to a three tie length).

Figure 10:
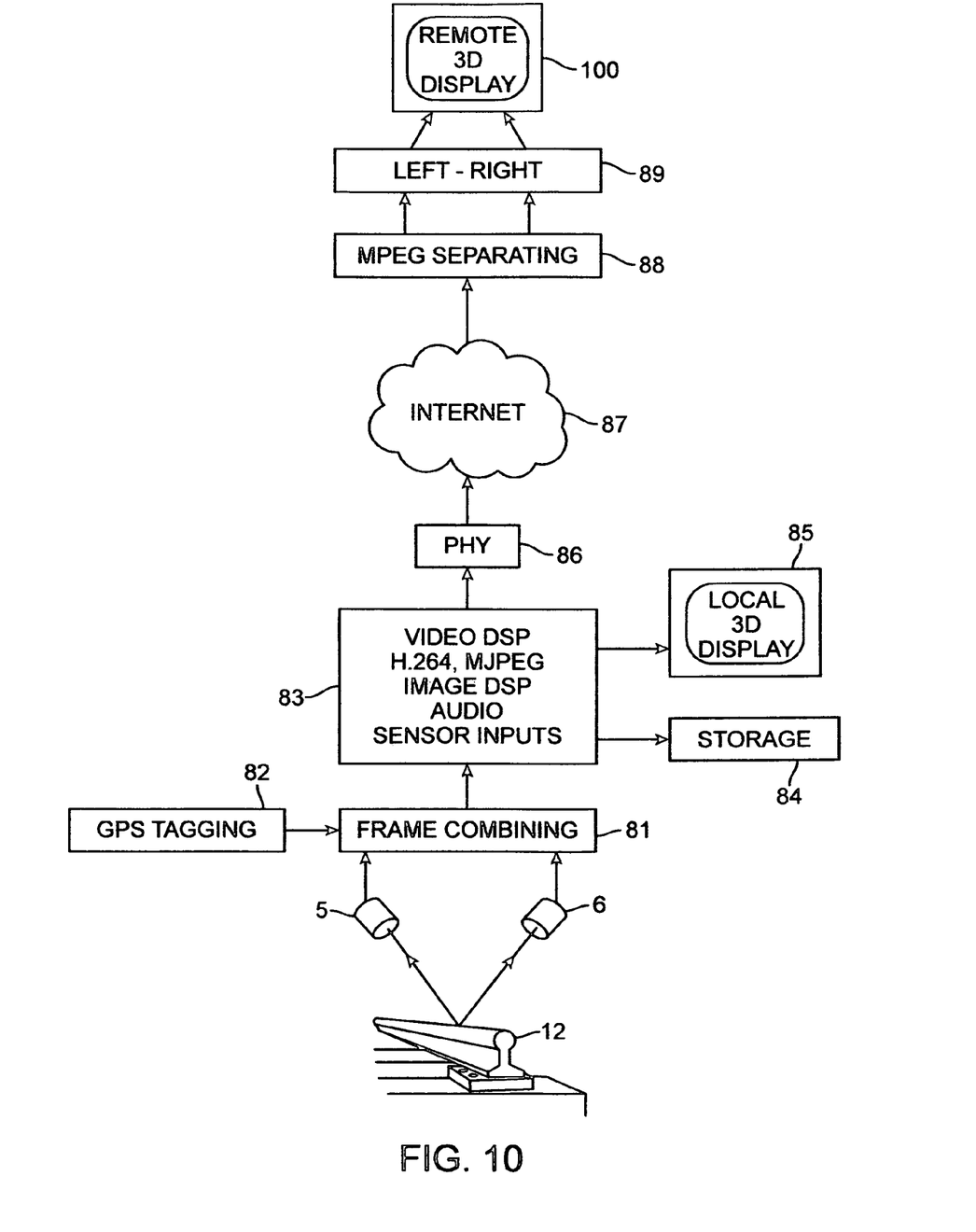
FIG. 10 shows a flow of images from an object (rail 12) through matched cameras 5 and 6 up to a remote 3D display 90. The images are first combined in a specialized 3D chip 81 which synchronizes the frames into a single stream. Every frame is numbered and its geographical coordinates are tagged by GPS system 82. The images are processed in a compact on-board computer 83, which compresses the images. The images can either be viewed locally or sent over the Internet for viewing remotely on a display 100.

FIG. 10 shows the processing for each camera pair. In this figure cameras 5 and 6 are looking at a section of rail 12. The camera outputs are combined in a 3D video preprocessor 81, in which selected frames are tagged with their GPS coordinates from a Global Positioning System 82. This output is fed into processor 83 which has internal DSP functions to create enhanced image stabilization, dual stream H.264 encoding (which handles data compression), MJPEG encoding, an RS-485/RS-232 output to local storage 84, an HDMI output (for local 3D viewing on display 85), and an output to a Physical Layer chip 86 for transmission over the Internet 87 (for remote 3D viewing). The processor 83 also has an output to a wireless connection which uses 802.11n for 4G communication speeds. From the Internet 87 there is added an MPEG separating module 88 to break the data into left and right streams for viewing in a remote display 100.

The frame combiner 81 and the processor 83 have the capacity to capture 500 MegaPixels per second and process full 3DHD of 1080p60 to a local display 85. The rate at which scenes can unfold on remote display 100 is limited only by the vagaries of the Internet.

In this description we are following MPEG-4, which is a collection of methods defining compression of audio and visual (AV) digital data beginning in 1998. It was at that time designated a standard for a group of audio and video coding formats and related technology agreed upon by the ISO/IEC Moving Picture Experts Group (MPEG) under the formal standard ISO/IEC 14496. In July 2008, the ATSC standards were amended to include H.264/MPEG-4 AVC compression and 1080p at 50, 59.94, and 60 frames per second (1080p50 and 1080p60)—the last of which is used here. These frame rates require H.264/AVC High Profile Level 4.2, while standard HDTV frame rates only require Level 4.0. Uses of MPEG-4 include compression of AV data for web (streaming media) and CD distribution voice (telephone, videophone) and broadcast television applications). We could equally use any other protocol (or combination of protocols) suitable for transferring high-speed data over airwaves or land-lines In FIG. 10 the output to the display 85 can also come from local storage 84.

We note now how scenes actually viewed are compared with templates. Two types of recognition are provided. The first is for the ties where anomalies must be analyzed by their presence. The second is for the rails where items must (mostly) be recognized by their absence.

For the rails we adapt a training algorithm, such as that described in such publications as C. M. Bishop's in *Pattern Recognition and Machine Learning* (2006), which can be simplified knowing that the shape, size and location of the bolts, fishplates, Pandrol clips and baseplates are fixed. Into the algorithm is built the expectation that these items will recur regularly, intact and properly located. If not, in each instance of absence an alarm is set.

For the ties the training is more complex. The templates provided for each track section describe if ties are wooden, steel or concrete. However we do not know a priori whether they will be visible. They are often covered in ballast, vegetation or loose metal. They are often skewed. Nor do we know a priori the shape and size of the anomalies.

Therefore training consists of running the cameras over sample sections of tracks until certain patterns emerge then to use those patterns to guide the definition of anomalies.

For example, the leading edge of a tie 18 or the leading edge of the baseplate 15, may be used to trigger a frame in cameras 1 and 2. In the case of a skewed and obscured tie the average of the leading edge of both left and right baseplates can be used to trigger a frame as well as to register its GPS coordinates.

While the invention has been described and illustrated generally as a method for recognizing, inspecting and measuring three dimensional objects such as railroad ties and rails, in fact to those skilled in the art, the techniques of this invention can be understood and used as means for creating and perfecting three-dimensional recognition, inspection and measurement tools for various subjects throughout the electro-magnetic spectrum and beyond.

The techniques of this invention may be applied whether cameras are moving relative to fixed objects, or objects are moving relative to fixed cameras.

It may be understood in this invention that although specific terms are employed, they are used in a generic and descriptive sense and must not be construed as limiting. The scope of the invention is set out in the appended claims.

I claim:

1. A method of detecting worn and defective surfaces on objects needing optical inspection comprising the steps of:
   moving an array of imaging devices relative to said objects over a pathway, at least one pair of said imaging devices positioned as a first and second imaging device and having an included angle about a reference center plane to generate corresponding uncorrected first and second images of said objects;
   capturing a sequence of image data formed as said imaging devices move over said pathway;
   forming a sequence of corrected 3D images from said uncorrected first and second images by performing an alignment of said first and second images mechanically and/or electronically;
   for each said pair of imaging devices, comparing at least one of said first or said second corrected 3D images against a reference image to identify a defective or worn surface of said object needing inspection;
   where said worn and defective surface is on a railroad track component including at least one of: a rail, a rail edge, nuts, tie-plates, base-plates, pandrol clips, or ties.

2. The method as in claim 1 where said comparing at least one of said first or said second corrected 3D image against a reference image is a comparison between said first and said second corrected 3D images.

3. The method as in claim 1 wherein said alignment includes the steps of:
   coarsely aligning said imaging devices by means of physical manipulation; and
   finely aligning said imaging devices by means of image matching software examining features in said images to achieve said alignment.

4. The method as in claim 1 where said comparing said first corrected 3D image and said second corrected 3D image is a comparison between said first corrected 3D image and a corresponding reference first image, and/or a comparison between said second corrected 3D image and a reference second image.

5. The method as in claim 4 wherein said imaging devices detect a surface defect such as a crack or erosion by detecting the offset of an imaged feature in at least one of said pair of images.

6. The method as in claim 5 wherein the depth of said defect is proportional to said offset in said at least one of said pairs of images.

7. The method of claim 1 where said comparison includes a step of storing said first and second corrected 3D image as a stereo pair.

8. The method of claim 7 where said step of storing includes location information associated with said defective or worn surface.

9. The method of claim 8 where said location information is a GPS coordinate acquired at the time said uncorrected 3D images were acquired.

10. The method of claim 1 where each said first and second pair of imaging devices is oriented to intersect a common point of a potentially worn or defective surface to be inspected.

11. The method of claim 1 where said corrected 3D images are generated by aligning said first and second image by minimizing ESSD(u) where:

$$ESSD(u)=\Sigma i[I1(xi+u)-I0(xi)]^2=\Sigma i(ei)^2$$

and u=(u, v) is a feature displacement on orthogonal axes and ei=I1 (xi+u)−I0(xi) is the error function or feature displacement offset within feature areas.

12. The method of claim 1 where said worn and defective surface is at least one of cracks, erosion, brinelling, or spalling in a rail.

13. An imaging device comprising:
a plurality of imaging detectors arranged in pairs and mounted on a structure to allow viewing of said fixed objects from different perspectives;
said pairs of detectors aligned in pairs or in a plurality for 3D viewing of said fixed objects, each said pair of detectors separated by a distance sufficient to resolve the depth of a defect by a variance in an imaged feature from a reference dimension;
said rigid structure providing mounting for at least one pair of detectors aligned parallel to a structure to be imaged and also at least one pair of detectors arranged substantially perpendicular to said one pair of image detectors;
wherein said certain fixed objects are railroad ties and other fixed objects include at least one of: rails, baseplates, clips, ties, or other objects associated with the tracks of a railroad.

14. The imaging device as in claim 13 where at least one said pair of detectors compare a corresponding pair of images from said pair of detectors to identify a defect.

15. The imaging device as in claim 13 where said pair of detectors compares acquired images to reference images.

16. The imaging device as in claim 13 where at least one said pair of detectors detect a surface defect such as a crack or erosion by detecting the offset of an imaged feature in at least one of a pair of images acquired by said pair of detectors.

17. The imaging device as in claim 16 where the depth of a detected defect is proportional to said offset in said at least one of said detectors.

18. The imaging device as in claim 13 wherein said imaging means and processing means calculate defect metrics including depth, erosion, and track width as said plurality of image detectors is moved over said objects.

* * * * *